United States Patent
Waddell et al.

(10) Patent No.: US 8,861,167 B2
(45) Date of Patent: Oct. 14, 2014

(54) BIPOLAR IONIZATION DEVICE

(75) Inventors: Charles Houston Waddell, Roanoke, VA (US); Joseph Anton Christiansen, Savannah, GA (US)

(73) Assignee: Global Plasma Solutions, LLC, Savannah, GA (US)

( * ) Notice: Subject to any disclaimer, the term of this patent is extended or adjusted under 35 U.S.C. 154(b) by 377 days.

(21) Appl. No.: 13/188,764

(22) Filed: Jul. 22, 2011

(65) Prior Publication Data

US 2012/0287551 A1 Nov. 15, 2012

Related U.S. Application Data

(60) Provisional application No. 61/485,178, filed on May 12, 2011.

(51) Int. Cl.

| | | |
|---|---|---|
| B03C 3/45 | (2006.01) | |
| B03C 3/49 | (2006.01) | |
| H01T 23/00 | (2006.01) | |
| F24F 3/16 | (2006.01) | |
| B03C 3/38 | (2006.01) | |
| B03C 3/86 | (2006.01) | |
| B03C 3/70 | (2006.01) | |
| A61L 2/14 | (2006.01) | |
| F26B 21/00 | (2006.01) | |
| B03C 3/41 | (2006.01) | |

(52) U.S. Cl.
CPC . *A61L 2/14* (2013.01); *B03C 3/383* (2013.01); *B03C 3/86* (2013.01); *B03C 3/70* (2013.01); *F26B 21/003* (2013.01); *B03C 3/41* (2013.01); *B03C 2201/10* (2013.01); *B03C 2201/08* (2013.01)

USPC .............................. 361/231; 361/213; 96/49

(58) Field of Classification Search
CPC ........... H01T 23/00; F24F 3/166; B03C 3/45; B03C 3/49
USPC ........................................ 361/230, 231; 96/49
See application file for complete search history.

(56) References Cited

U.S. PATENT DOCUMENTS

| | | | |
|---|---|---|---|
| 3,321,621 A | * | 5/1967 | Bustamante .................. 362/430 |
| 3,867,324 A | | 2/1975 | Clendinning et al. |
| 3,961,175 A | | 6/1976 | Otagoshi |
| 3,997,304 A | | 12/1976 | Carr |
| 4,191,818 A | | 3/1980 | Illers et al. |
| 4,244,709 A | | 1/1981 | Chang |

(Continued)

FOREIGN PATENT DOCUMENTS

AT          2000/01320      *    7/2000   ............. B01D 46/50

OTHER PUBLICATIONS 5,190,885, 03/1993, (withdrawn).

(Continued)

*Primary Examiner* — Zeev V Kitov
(74) *Attorney, Agent, or Firm* — Seth L. Hudson; Clements Bernard PLLC

(57) ABSTRACT

The present invention provides methods and systems for a bipolar ionization device that includes an electrically insulated base, a power input terminal, an anode engaged to the base and the power input terminal, a cathode that partially circumscribes the anode, and plurality of tines extending perpendicularly from the anode having a lower portion and a top portion, wherein the lower portion is engaged to the anode and is wider than the top portion.

14 Claims, 3 Drawing Sheets

(56) References Cited

U.S. PATENT DOCUMENTS

| | | | |
|---|---|---|---|
| 4,250,504 A | 2/1981 | Eichelberger | |
| 4,251,234 A | 2/1981 | Chang | |
| 4,252,395 A | 2/1981 | Ward et al. | |
| 4,265,641 A | 5/1981 | Natarajan | |
| 4,400,498 A | 8/1983 | Konishi et al. | |
| 4,423,701 A | 1/1984 | Nath et al. | |
| 4,439,552 A | 3/1984 | Dedolph | |
| 4,496,375 A | 1/1985 | Le Vantine | |
| 4,525,272 A * | 6/1985 | Henson .......................... | 210/149 |
| 4,618,909 A | 10/1986 | Sanders | |
| 4,757,422 A | 7/1988 | Bossard et al. | |
| 4,762,884 A | 8/1988 | Goyert et al. | |
| 4,797,447 A | 1/1989 | Gergen et al. | |
| 4,900,776 A | 2/1990 | Bock et al. | |
| 4,906,687 A | 3/1990 | Modic | |
| 4,974,257 A | 11/1990 | Ibanez et al. | |
| 5,015,412 A | 5/1991 | Zeman | |
| 5,017,876 A * | 5/1991 | Wright et al. ................. | 324/464 |
| 5,096,939 A | 3/1992 | Mor | |
| 5,159,053 A | 10/1992 | Kolycheck et al. | |
| 5,187,214 A | 2/1993 | Govindan | |
| 5,231,290 A | 7/1993 | Czirr et al. | |
| 5,249,094 A | 9/1993 | Hayakawa et al. | |
| 5,258,649 A | 11/1993 | Tanaka et al. | |
| 5,262,336 A | 11/1993 | Pike, Jr. et al. | |
| 5,278,758 A | 1/1994 | Perry et al. | |
| 5,342,889 A | 8/1994 | Sullivan et al. | |
| 5,409,673 A | 4/1995 | Mausgrover et al. | |
| 5,420,751 A | 5/1995 | Burns | |
| 5,433,927 A | 7/1995 | Mausgrover et al. | |
| 5,455,760 A | 10/1995 | Bilas et al. | |
| 5,476,121 A | 12/1995 | Yoshikawa et al. | |
| 5,508,099 A | 4/1996 | Incorvia | |
| 5,597,864 A | 1/1997 | Leiss | |
| 5,604,445 A | 2/1997 | Desai et al. | |
| 5,617,629 A | 4/1997 | Ekstrom | |
| 5,621,258 A | 4/1997 | Stevenson | |
| 5,863,466 A | 1/1999 | Mor | |
| 5,870,275 A | 2/1999 | Shiono et al. | |
| 5,945,781 A | 8/1999 | Valentian | |
| 6,130,507 A | 10/2000 | Maishev et al. | |
| 6,162,709 A | 12/2000 | Raoux et al. | |
| 6,197,486 B1 | 3/2001 | Majumdar et al. | |
| 6,207,361 B1 | 3/2001 | Greener et al. | |
| 6,228,149 B1 | 5/2001 | Alenichev et al. | |
| 6,231,788 B1 | 5/2001 | Patel | |
| 6,238,466 B1 | 5/2001 | Rousseau et al. | |
| 6,248,262 B1 | 6/2001 | Kubotera et al. | |
| 6,261,342 B1 | 7/2001 | Rousseau et al. | |
| 6,302,504 B1 | 10/2001 | Imanaka et al. | |
| 6,358,573 B1 | 3/2002 | Raoux et al. | |
| 6,391,048 B1 | 5/2002 | Ginn et al. | |
| 6,447,329 B1 | 9/2002 | Yang | |
| 6,468,275 B1 | 10/2002 | Wampler et al. | |
| 6,471,136 B1 * | 10/2002 | Chatterjee et al. ............ | 237/2 B |
| 6,508,982 B1 | 1/2003 | Shoji | |
| 6,528,572 B1 | 3/2003 | Patel et al. | |
| 6,534,422 B1 | 3/2003 | Ichikawa et al. | |
| 6,540,945 B2 | 4/2003 | Kubotera et al. | |
| 6,596,199 B2 | 7/2003 | Patel | |
| 6,621,684 B2 | 9/2003 | Shimamoto et al. | |
| 6,681,587 B2 | 1/2004 | Murase | |
| 6,740,410 B2 | 5/2004 | Fahey et al. | |
| 6,825,727 B1 | 11/2004 | Hill | |
| 6,826,213 B1 | 11/2004 | Edwards | |
| 6,828,729 B1 | 12/2004 | Owens et al. | |
| 6,837,887 B2 | 1/2005 | Woloszko et al. | |
| 6,837,888 B2 | 1/2005 | Ciarrocca et al. | |
| 6,850,403 B1 | 2/2005 | Gefter et al. | |
| 6,863,869 B2 | 3/2005 | Lau et al. | |
| 6,872,501 B2 | 3/2005 | Majumdar et al. | |
| 6,896,853 B2 | 5/2005 | Lau et al. | |
| 6,902,604 B2 | 6/2005 | Heckel et al. | |
| 6,911,186 B2 | 6/2005 | Taylor et al. | |
| 6,913,637 B2 | 7/2005 | Kim | |
| 6,919,053 B2 | 7/2005 | Joannou | |
| 6,922,021 B2 | 7/2005 | Espiau et al. | |
| 6,949,096 B2 | 9/2005 | Davison et al. | |
| 6,958,474 B2 | 10/2005 | Laprade et al. | |
| 6,970,343 B2 | 11/2005 | Hayashi et al. | |
| 6,974,560 B2 | 12/2005 | Taylor et al. | |
| 6,984,987 B2 | 1/2006 | Taylor et al. | |
| 7,004,107 B1 | 2/2006 | Raoux et al. | |
| 7,018,567 B2 | 3/2006 | Murray | |
| 7,026,177 B2 | 4/2006 | Laprade | |
| 7,026,432 B2 | 4/2006 | Charati et al. | |
| 7,122,794 B1 | 10/2006 | Miller et al. | |
| 7,141,787 B2 | 11/2006 | Laprade | |
| 7,156,898 B2 | 1/2007 | Jaisinghani | |
| 7,177,133 B2 | 2/2007 | Riskin | |
| 7,202,322 B2 | 4/2007 | Vedula et al. | |
| 7,212,129 B2 | 5/2007 | Barber et al. | |
| 7,218,501 B2 | 5/2007 | Keely | |
| 7,237,352 B2 | 7/2007 | Keely et al. | |
| 7,256,979 B2 | 8/2007 | Sekoguchi et al. | |
| 7,258,729 B1 | 8/2007 | Barsimanto et al. | |
| 7,262,702 B2 | 8/2007 | Barber et al. | |
| 7,283,027 B2 | 10/2007 | Batteux et al. | |
| 7,291,207 B2 | 11/2007 | Taylor et al. | |
| 7,309,386 B2 | 12/2007 | Wu et al. | |
| 7,309,727 B2 | 12/2007 | Elkovitch et al. | |
| 7,311,762 B2 | 12/2007 | Taylor et al. | |
| 7,318,856 B2 | 1/2008 | Taylor et al. | |
| 7,319,018 B2 | 1/2008 | Pandey et al. | |
| 7,325,744 B2 | 2/2008 | Porter | |
| 7,331,957 B2 | 2/2008 | Woloszko et al. | |
| 7,339,164 B2 | 3/2008 | Miller et al. | |
| 7,354,988 B2 | 4/2008 | Charati et al. | |
| 7,364,873 B2 | 4/2008 | Pandey et al. | |
| 7,368,709 B2 | 5/2008 | Guevremont | |
| 7,371,354 B2 | 5/2008 | Lau | |
| 7,381,944 B2 | 6/2008 | Cameron et al. | |
| 7,393,385 B1 | 7/2008 | Coffey et al. | |
| 7,399,959 B2 | 7/2008 | Miller et al. | |
| 7,462,656 B2 | 12/2008 | Keulen et al. | |
| 7,483,225 B2 | 1/2009 | Shimo | |
| 7,498,369 B2 | 3/2009 | Whear et al. | |
| 7,503,796 B2 | 3/2009 | Luettermann et al. | |
| 7,598,489 B2 | 10/2009 | Miller et al. | |
| 7,621,986 B2 | 11/2009 | Bologa et al. | |
| 7,697,258 B2 | 4/2010 | Vernitskiy et al. | |
| 7,714,282 B2 | 5/2010 | Guevremont et al. | |
| 7,892,501 B2 | 2/2011 | Parker et al. | |
| 7,897,118 B2 | 3/2011 | Taylor et al. | |
| 7,897,281 B2 | 3/2011 | Yamakawa et al. | |
| 7,906,080 B1 | 3/2011 | Botvinnik | |
| 7,914,704 B2 | 3/2011 | Yamakawa et al. | |
| 7,959,869 B2 | 6/2011 | Taylor et al. | |
| 8,106,367 B2 | 1/2012 | Riskin | |
| 8,107,223 B2 | 1/2012 | Lipka et al. | |
| 2003/0206837 A1 | 11/2003 | Taylor | |
| 2003/0206839 A1 | 11/2003 | Taylor | |
| 2003/0206840 A1 | 11/2003 | Taylor | |
| 2004/0118276 A1 | 6/2004 | Kim | |
| 2004/0251909 A1 | 12/2004 | Taylor et al. | |
| 2005/0031503 A1 * | 2/2005 | Fox et al. .................. | 422/186.04 |
| 2005/0158219 A1 | 7/2005 | Taylor et al. | |
| 2005/0163669 A1 | 7/2005 | Taylor et al. | |
| 2005/0183576 A1 | 8/2005 | Taylor et al. | |
| 2006/0016333 A1 | 1/2006 | Taylor et al. | |
| 2006/0018076 A1 | 1/2006 | Taylor et al. | |
| 2006/0018809 A1 | 1/2006 | Taylor et al. | |
| 2006/0018811 A1 | 1/2006 | Taylor et al. | |
| 2006/0150816 A1 | 7/2006 | Jaisinghani | |
| 2006/0222562 A1 | 10/2006 | Miller et al. | |
| 2007/0023631 A1 | 2/2007 | Takats et al. | |
| 2007/0045530 A1 | 3/2007 | Miller et al. | |
| 2007/0148061 A1 | 6/2007 | Lau et al. | |
| 2007/0158578 A1 | 7/2007 | Vernitskiy et al. | |
| 2010/0067164 A1 | 3/2010 | Goudy, Jr. | |
| 2010/0176290 A1 | 7/2010 | Vidal-De-Miguel | |
| 2010/0247389 A1 * | 9/2010 | Abate .......................... | 422/121 |

(56) References Cited

U.S. PATENT DOCUMENTS

2010/0282083 A1 11/2010 Edwards
2011/0097507 A1 4/2011 Dick et al.

OTHER PUBLICATIONS

Al-Ahmady, Kaiss K., Indoor Ozone, Florida Journal of Environmental Health, Jun. 1997, pp. 8-12.

American Lung Association, Residential Air Cleaning Devices: Types, Effectiveness, and Health Impact, Jan. 1997, Washington, D.C.

American Society of Heating, Refrigerating, and Air Conditioning Engineers (ASHRAE), ASHRAE Handbook of Fundamentals, 1989, p. 12.1-12.6, Atlanta, GA.

Boeniger, Mark F., Use of Ozone Generating Devices to Improve Indoor Air Quality, American Industrial Hygiene Association Journal, 1995, pp. 590-598, vol. 56, Issue 6.

Dunston, N.C.; Spivak, S.M., A Preliminary Investigation of the Effects of Ozone on Post-Fire Volatile Organic Compounds, Journal of Applied Fire Science, 1997, pp. 231-242, vol. 6, No. 3.

Dyas, A; Boughton, B.J.; Das, B.C., Ozone Killing Action Against Bacterial and Fungal Species; Microbiological Testing of a Domestic Ozone Generator, Journal of Clinical Pathology, Oct. 1983, pp. 1102-1104, vol. 36.

Esswein, Eric J.; Boeniger, Mark F., Effects of an Ozone-Generating Air-Purifying Device on Reducing Concentrations of Formaldehyde in Air, Applied Occupational Environmental Hygiene, 1994, pp. 139-146, vol. 9, Issue 2.

Foarde, K.; Van Osdell, D.; and Steiber, R., Investigation of Gas-Phase Ozone as a Potential Biocide, Applied Occupational Environmental Hygiene, 1997, pp. 535-542, vol. 12, Issue 4.

Hayes, S.R., Use of an Indoor Air Quality Model (IAQM) to Estimate Indoor Ozone Levels, Journal of Air and Waste Management Association, 1991, pp. 161-170, vol. 41, Issue 2.

Pierce, Mark W.; Janczewski, Jolanda N., Roethlisberger. Brian; Pelton, Mike; and Kunstel, Kristen, Effectiveness of Auxiliary Air Cleaners in Reducing ETS Components in Offices, ASHRAE Journal, Nov. 1996, pp. 51-57.

Salls, Carroll M., The Ozone Fallacy in Garage Ventilation, The Journal of Industrial Hygiene, Dec. 1927, pp. 503-511, vol. 9, Issue 12.

Sawyer, W. A.; Beckwith, Helen I.; and Skolfield, Esther M., The Alleged Purification of Air by the Ozone Machine, Journal of the American Medical Association, Sep. 27, 1913, pp. 1013-1015, vol. 61, No. 13.

Shaughnessy, Richard, J.; Levetin, Estelle; Blocker, Jean; and Sublette, Kerry L., Effectiveness of Portable Indoor Air Cleaners: Sensory Testing Results, Indoor Air, Journal of the International Society of Indoor Air Quality and Climate, 1994, pp. 179-188, vol. 4.

Shaughnessy, R.J.; and Oatman, L., The Use of Ozone Generators for the Control of Indoor Air Contaminants in an Occupied Environment, Proceedings of the ASHRAE Conference IAQ '91, Healthy Buildings, 1991, pp. 318-324, ASHRAE, Atlanta, GA.

U.S. Environmental Protection Agency (US EPA), Ozone Generators in Indoor Air Settings, Report prepared for the Office of Research and Development by Raymond Steiber, National Risk Management Research Laboratory, U.S. EPA, 1995, Research Triangle Park, EPA-600/R-95-154.

U.S. Environmental Protection Agency (US EPA), Air Quality Criteria for Ozone and Related Photochemical Oxidants, 1996, Research Triangle Park, NC: National Center for Environmental Assessment—RTP Office; Report Nos. EPA/600/P-93/004aF-cF, 3v., NTIS, Springfield, VA; PB-185582, PB96-185590 and PB96-185608.

U.S. Environmental Protection Agency (US EPA), Review of National Ambient Air Quality Standards for Ozone: Assessment of Scientific and Technical Information, OAQPS Staff Paper, Office of Air Quality Planning and Standards, Jun. 1996, Research Triangle Park, NC, EPA-452/R-96-007.

Weschler, Charles J.; Bauer, Michael; and Koutrakis, Petros, Indoor Ozone and Nitrogen Dioxide: A Potential Pathway to the Generation of Nitrate Radicals, Dinitrogen Pentaoxide, and Nitric Acid Indoors, Environmental Science and Technology, 1992, pp. 179-184, vol. 26, Issue 1.

Weschler, Charles J.; Hodgson, Alfred T.; and Wooley, John D., Indoor Chemistry: Ozone, Volatile Organic Compounds, and Carpets, Environmental Science and Technology, Dec. 1992, pp. 2371-2377, vol. 26, Issue 12.

Weschler, Charles J.; Shields, Helen C., Measurements of the Hydroxyl Radical in a Manipulated but Realistic Indoor Environment, Environmental Science and Technology, Nov. 1997, pp. 3719-3722, vol. 31, Issue 12.

Weschler, Charles J.; Shields, Helen C., Potential Reactions Among Indoor Pollutants, Atmospheric Environment, Nov. 1997, pp. 3487-3495, vol. 31, Issue 21.

Weschler, Charles J.; and Shields, Helen C., Production of the Hydroxyl Radical in Indoor Air, Environmental Science and Technology, Oct. 1996, pp. 3250-3268, vol. 30, Issue 11.

Weschler, Charles J.; Shields, Helen C.; and Naik, Datta V., Indoor Ozone Exposures, JAPCA Journal, Dec. 1989, pp. 1562-1568, vol. 39, Issue 12.

Weschler, Charles J.; Shields, Helen C.; and Naik, Datta V., The Factors Influencing Indoor Ozone Levels at a Commercial Building in Southern California: More that a Year of Continuous Observations, Tropospheric Ozone, Air and Waste Management Association, 1996, Pittsburgh.

Witheridge, William N. and Yaglou, Constantin P., Ozone in Ventilation—Its Possibilities and Limitations, ASHRAE Transactions, 1939, pp. 509-522, vol. 45.

Zhang, Junfeng and Lioy, Paul J., Ozone in Residential Air: Concentrations, I/O Ratios, Indoor Chemistry, and Exposures, Indoor Air, Journal of International Society of Indoor Air Quality and Climate, Jun. 1994, pp. 95-102, vol. 4.

\* cited by examiner

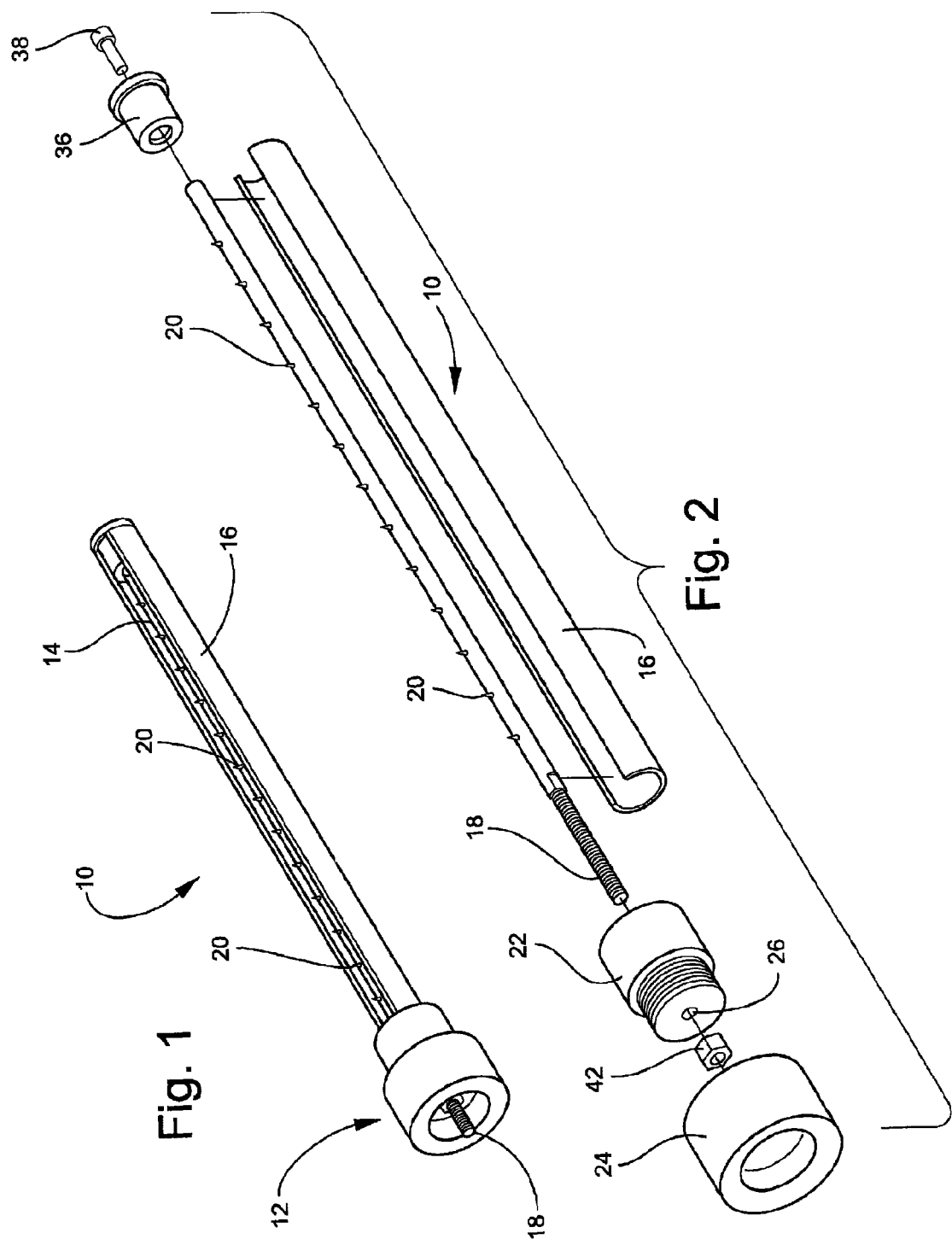

BIPOLAR IONIZATION DEVICE

CROSS REFERENCE TO RELATED PATENT APPLICATION

The current application claims the benefit of the earlier priority filing date of the provisional application Ser. No. 61/485,178, that was filed on May 12, 2011.

FIELD OF THE INVENTION

The present invention relates generally to a bipolar ionization device and more generally relates to a bipolar ionization device that includes an anode that is partially circumscribed by a cathode.

BACKGROUND OF THE INVENTION

Current ionization tubes utilize a cathode that is completely surrounded by a glass tube. The inside of the glass tube contains a wire mesh that serves as an anode. Glass by its very nature has a fragile structure and is prone to breaking. The glass tube in an ionization tube also produces a corona discharge, which minimizes the effect of the ionization tube and increases the amount of energy consumed during operation of ionization tube. The glass tube breaks down over time and must be replaced by the user and the replacement cost for such a tube is high. Additionally, the glass tube requires a voltage high enough to break down the dielectric strength of the glass, and during the break down process, a corona discharge is created, thus causing uncontrolled and undesirable ozone.

For example, U.S. Patent Application No. 2010/0247389 discloses a bipolar ionization tube that has a cathode that is completely surrounded by a glass tube. An anode is provided that circumscribes the interior wall of the glass tube.

There is a need for a bipolar ionization device that is not breakable, eliminates the need for expensive replacement parts, saves energy, provides higher output, and minimizes corona discharge

BRIEF SUMMARY OF THE INVENTION

The present invention is a bipolar ionization device that includes a base, a power input terminal, an anode engaged to the base, and a cathode that partially circumscribes the anode.

According to another embodiment of the present invention, the present invention includes a bipolar ionization device that has an electrically insulated base.

According to yet another embodiment of the present invention, the present invention includes a bipolar ionization device that has a power input terminal that is engaged to a power supply.

According to yet another embodiment of the present invention, the present invention includes a bipolar ionization device that has a power input terminal that is threaded for engagement to corresponding threads of a power supply.

According to yet another embodiment of the present invention, the present invention includes a bipolar ionization device that has an anode with tines that have a lower portion and a top portion, wherein the lower portion is engaged to the anode and is wider than the top portion.

According to yet another embodiment of the present invention, the present invention includes a bipolar ionization device that has a cathode that circumscribes an angle of greater than 180° with respect to the anode.

According to yet another embodiment of the present invention, the present invention includes a bipolar ionization device that has an electrically insulated base, a power input terminal, an anode engaged to the base and the power input terminal, a cathode that partially circumscribes the anode, and a plurality of tines extending perpendicularly from the anode having a lower portion and a top portion, wherein the lower portion is engaged to the anode and is wider than the top portion.

According to yet another embodiment of the present invention, the present invention includes a bipolar ionization device that has an electronically insulated end cap that is positioned between the anode and the cathode.

According to yet another embodiment of the present invention, the present invention includes a bipolar ionization device that has a base with a first portion and a second portion, whereby the first portion is engaged to the anode and the cathode and has a threaded outer body portion and the second portion has a threaded inner bore that engages the threaded first portion for forming a selectively secured arrangement.

According to yet another embodiment of the present invention, the present invention includes a bipolar ionization device that has an anode composed of brass.

According to yet another embodiment of the present invention, the present invention includes a bipolar ionization device that has a cathode composed of stainless steel.

According to yet another embodiment of the present invention, the present invention includes a bipolar ionization device that has a grounding ring engaged to the base.

According to yet another embodiment of the present invention, the present invention includes a bipolar ionization device that has a grounding ring and a conducting wire having a first end and a second end, wherein the first end is engaged to the grounding ring and the second end is engaged to a bracket.

According to yet another embodiment of the present invention, the present invention includes a bipolar ionization device that is a method of ionizing air that includes providing a bipolar ionization device that comprises a base, a power input terminal, an anode engaged to the base, and a cathode that partially circumscribes the anode, connecting the power input terminal to a power supply, and placing the bipolar ionization device in a stream of air.

According to yet another embodiment of the present invention, the present invention includes a bipolar ionization device that includes placing the bipolar ionization device into an HVAC duct.

BRIEF DESCRIPTION OF THE DRAWINGS

The present invention is illustrated and described herein with reference to the various drawings, in which like reference numbers denote like method steps and/or system components, respectively, and in which:

FIG. 1 is perspective view of the bipolar ionization device;

FIG. 2 is an exploded view of the bipolar ionization device;

DETAILED DESCRIPTION OF THE INVENTION

Figure 3:
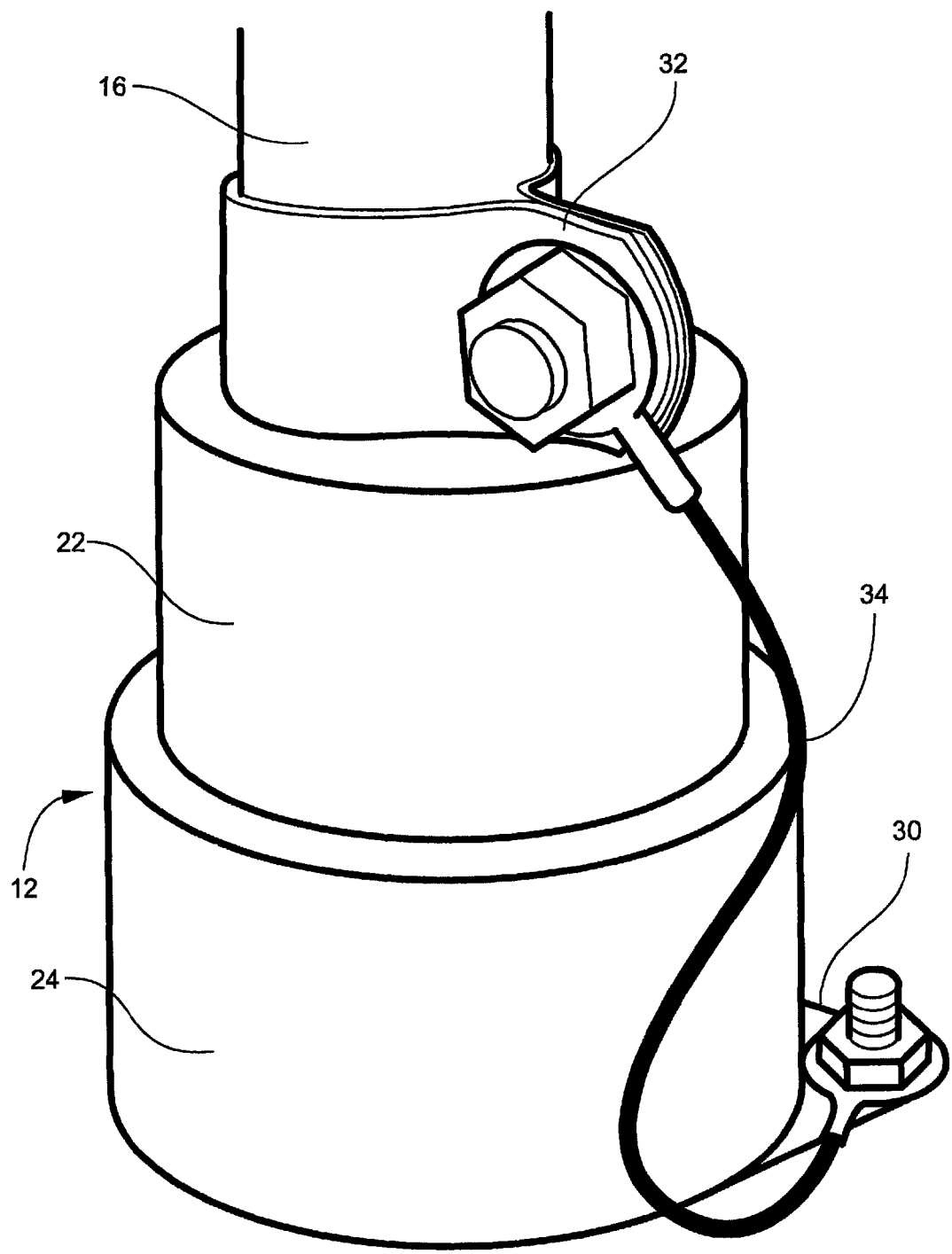
FIG. 3 is a perspective view of the bottom portion of the bipolar ionization device with a grounded bracket and wire.

Referring now specifically to the drawings, a bipolar ionization device is illustrated in FIGS. 1 and 2 and is shown generally at reference numeral 10. The bipolar ionization device 10 generally comprises an electrically insulated base 12, an anode 14, a cathode 16, and a power input terminal 18. The anode 14 is a generally cylindrical tube that extends from the base 12. The cathode 16 is spaced-apart from the anode 14 and partially circumscribes the anode 14. The power input terminal 18 may be integral with the anode 14 or may be engaged to the anode 14. As illustrated in FIG. 1, the power input terminal 18 extends through the base 12 and extends a distance from the base 12 for engaging to a power supply.

Figure 4:
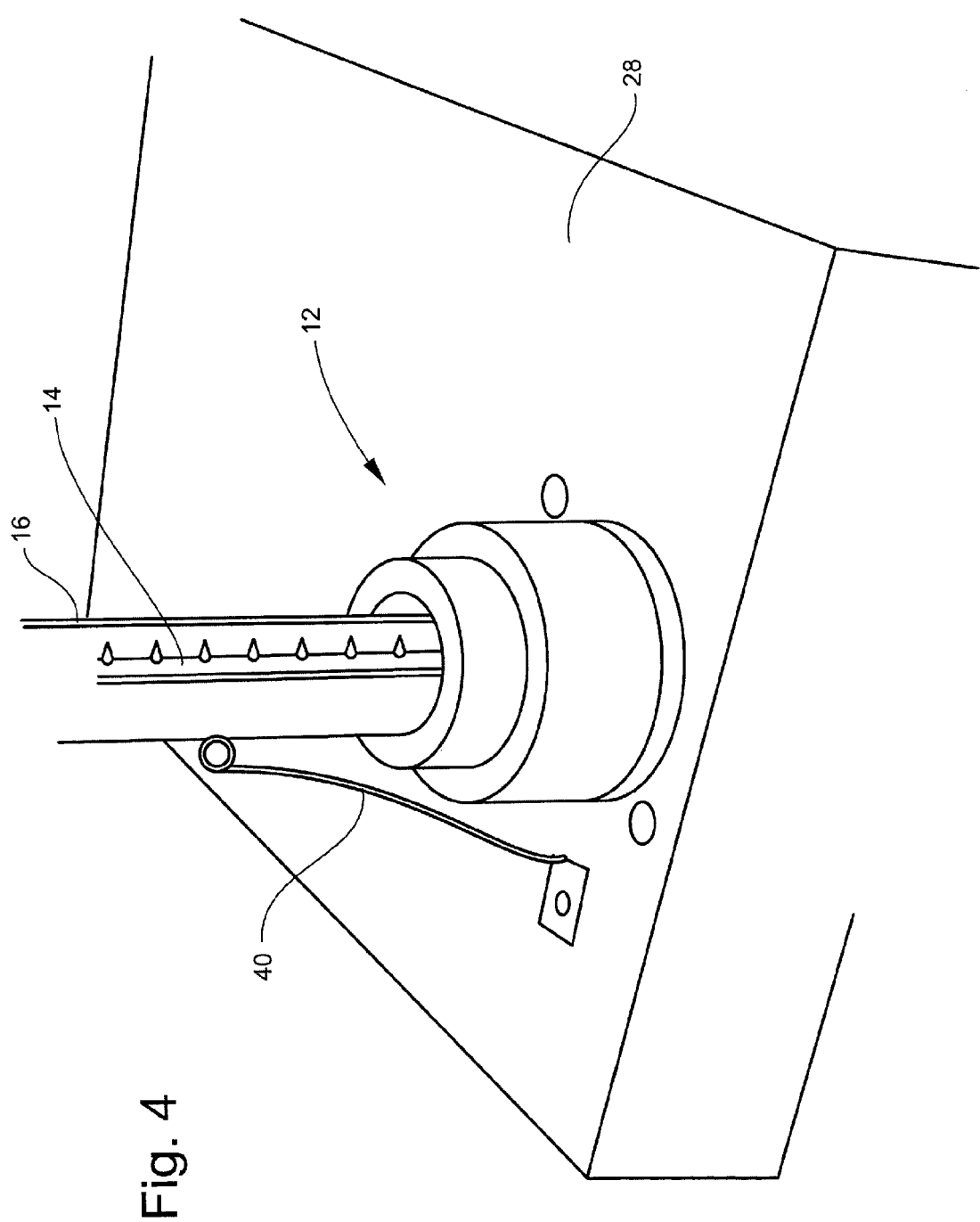
FIG. 4 is a perspective view of the bottom portion of the bipolar ionization device that is engaged to a power supply with a grounded biasing element.

As illustrated in FIG. 2, the power input terminal 18 and the anode 14 are integral, meaning the power input terminal 18 is formed from the anode 14. The power input terminal 18 has a top end and a bottom end and contains threads for receiving corresponding threads of a high voltage alternating current power supply 28 and forming a selectively secured arrangement between the power input terminal 18 and the power supply 28. In one exemplary embodiment, the power input terminal 18 is machined into the bottom end of the anode 14. Preferably, this is done by turning the end of the anode 14 on a lathe. The power input terminal 18, as illustrated in FIG. 2, extends a distance away from the base 12 to allow for connection to the power supply 28. As illustrated in FIG. 4, the power input terminal 18 is screwed into the power supply 28 for selectively securing the bipolar ionization device 10 to the power supply 28. The power supply 28 similar to the one illustrated in FIG. 4 can be purchased from Bioclimatic, Plasma Air, Atmos Air, or Bentax. It should be noted that alternatively, the power input terminal 18 may be a plug-in or a stab-on type connector or the like.

The top end of the anode 14 contains a plurality of tines 20. The tines 20 may be embedded into bores that are spaced along the axial length of the top end of the anode 14. The tines 20 contain a base and an upper end. The base of the tines 20 is larger than the upper end. Preferably, the upper end of each tine 20 has a point. In other words, the tines 20 have a base that is embedded into a bore spaced along the axial length of the top end of the anode 14 and the top end of the tines 20 forms a point. The diameter of the tines 20 from the base to the top end gradually decreases until a point is formed. The tines 20 may be composed of stainless steel, gold, titanium, brass, or any other conductive, but oxidation resistant material.

The cathode 16 is annular in shape and is designed to partially circumscribe the anode 14. The diameter of the cathode 16 is slightly larger than the diameter of the anode 14, thus providing a spaced apart relationship when the anode 14 is placed within the cathode 16. The term partially circumscribes is intended to mean that the cathode 16 does not fully encompass the anode 14. The cathode 16 has a first side and a second side that are not engaged, but are spaced apart. In one embodiment, the cathode 16 partially circumscribes the anode 14 at an angle of greater than 180° with respect to the anode 14, but does not circumscribe an angle of 360° with respect to the anode 14.*tu*

The base 12 may be any type of base 12 that retains the anode 14. As illustrated in FIG. 2, the base 12 contains a mounting base 22 and a retention base 24. The mounting base 22 contains a bore 26 that extends through the center of the mounting base 22. The bore 26 may be threaded for receiving the correspondingly threaded bottom end of the anode 14. Alternatively, the bore 26 contains no threads and allows the anode 14 to extend there through uninhibited. A correspondingly threaded nut 42 may be utilized to selectively secure the anode 14 to the base 12, and in particular the mounting base 22 of the base 12. The mounting base 22 contains a top portion and a bottom portion. The bottom portion of the mounting base 22 is threaded and the inside of the retention base 24 contains corresponding threads for selectively securing the mounting base 22 to the retention base 24.

In one embodiment, a conductive ring 30 is engaged to the base 12 and is disposed between the power supply 28 and the retention base 24. As illustrated in FIG. 3, the conductive ring 30 contains a metal bracket 32 that circumscribes the cathode 16. In an embodiment as illustrated in FIG. 3, a grounding wire 34 having a first end and a second end is shown, wherein the first end is engaged to the bracket 32 and the second end is engaged to the conductive ring 30. The first end and the second end of the grounding wire 34 contain a circular metallic lead with a central bore, as shown in FIG. 3. The bracket 32 and conductive ring 30 each contain a conductive screw that is received within the central bore of the metallic lead on the first end and the second end of the grounding wire 34. A correspondingly threaded nut is disposed on the screw for retaining the grounding wire 34 to the conductive ring 30 and bracket 32.

In lieu of the conductive ring 30 and bracket 32, the power supply 28 may contain a grounded biasing element 40. The grounded biasing element 40 has a bottom portion and a top portion, wherein the bottom portion is engaged to the power supply 28 and the top portion is engaged to the cathode 16, as illustrated in FIG. 4.

The top of the cathode 16 is retained in a spaced-apart relationship to the anode 14 with a spacer 36. The spacer 36 may be composed of rubber or another electrically insulated material. That spacer 36 comprises a circular body with a raised shelf at one end. The spacer 36 also contains a hollow bore extending through the center of the spacer 36. The hollow bore of the spacer 36 has a diameter slightly larger than the diameter of the anode 14 for receiving the upper portion of the anode 14 into the hollow bore. The circular body of the spacer 36 has a diameter slightly smaller than the diameter of the cathode 16, allowing the cathode 16 to fit around the circular body of the spacer 36. The spacer 36 is designed to receive a retention pin 38 that is received within the upper portion of the hollow bore of the spacer 36 and selectively secures the anode 14 to the spacer 36.

The anode 14 may be composed of any material that can conduct electricity. In one embodiment of the present invention, the anode 14 may be composed of brass or any other conductive, oxidation resistant material. The tines 20 can also be manufactured out of any material that conducts electricity, but in one embodiment the tines 20 are manufactured out of tungsten or stainless steel. The cathode 16 may be manufactured from stainless steel or any other conductive, oxidation resistant material. It should be noted that the cathode 16 and anode 14 may be of various sizes depending upon the uses and desires of the user and the size of the HVAC duct that bipolar ionization device 10 will be inserted.

In one use, the bipolar ionization device 10 may be installed in a heating, ventilation and air condition (HVAC) duct. The bipolar ionization device 10 is engaged to a power supply 28 and the bipolar ionization device 10 is inserted into a duct so that the air flows perpendicular to longitudinal length of the tines 20 on the anode 14. In other words, bipolar ionization device 10 should be positioned such that the tines 20 are upright in relation to the air flow and the air flow is able to flow between the tines 20.

During use, the power supply 28 supplies power to the power input terminal 18, and the electrons flow along the length of the anode 14. As the electrons progress upwards from the power input terminal 18 along the anode 14, the electrons contact the tines 20 and flow up the tines 20 from the base to the pointed upper end. When the electrons reach the pointed upper end of the tine 20, the electrons flow from the pointed upper end of the tine 20 of the anode 14 to the cathode 16 that partially circumscribes the anode 14. Not all of the electrons that flow from the anode 14 are collected by the cathode 16. Instead, the electrons that are not collected by the cathode 16 flow into the surrounding area and collide with air molecules and particles in the air stream, thus ionizing the air molecules and particles. The ionization of the air aids in cleaning the air, removing odors, and helps reduce pollutants.

The present invention is an advancement over prior art bipolar ionization tubes in that the present invention saves energy, minimizes corona discharge, eliminates costly replacement parts, and is not fragile or easily breakable.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A bipolar ionization device, comprising:
    an electrically insulated base;
    a power input terminal;
    an internal electrode engaged to the base and the power input terminal;
    an annular external electrode that partially circumscribes the internal electrode; and
    a plurality of tines extending perpendicularly from internal electrode having a lower portion and a top portion, wherein the lower portion is engaged to the internal electrode and is wider than the top portion.

2. The bipolar ionization device of claim 1, wherein the internal electrode has a top portion and a bottom portion and the bottom portion is threaded and serves as the power input terminal that is engaged to a power supply.

3. The bipolar ionization device of claim 1, wherein the internal electrode contains a threaded portion and a correspondingly threaded nut is engaged to the threaded portion for engaging the internal electrode to the electrically insulated base.

4. The bipolar ionization device of claim 1, wherein the external electrode circumscribes an angle of greater than 180° of the anode.

5. The bipolar ionization device of claim 1, further comprising an electrically insulated end cap that is positioned between the internal electrode and external electrode.

6. The bipolar ionization device of claim 1, wherein the base consists of a first portion and a second portion, whereby the first portion is engaged to the internal electrode and external electrode and has a threaded outer body portion and the second portion has a threaded inner bore that engages the threaded first portion for forming a selectively secured arrangement.

7. The bipolar ionization device of claim 1, wherein the internal electrode is composed of brass.

8. The bipolar ionization device of claim 1, wherein the external electrode is composed of stainless steel.

9. The bipolar ionization device of claim 1, further comprising a grounding ring that circumscribes the external electrode.

10. The bipolar ionization device of claim 1, further comprising a grounding ring and a conducting wire having a first end and a second end, wherein the first end is engaged to the grounding ring and the second end is engaged to a grounded structure.

11. A method of ionizing air, comprising:
    providing bipolar ionization device that comprises a base, a power input terminal, an internal electrode engaged to the base, and an annular external electrode that partially circumscribes the internal electrode;
    connecting the power input terminal to a power supply; and
    placing the bipolar ionization device in a stream of air.

12. The method of ionizing air of claim 11, further providing a plurality of tines extending perpendicularly from internal electrode having a lower portion and a top portion, wherein the lower portion is engaged to the internal electrode and is wider than the top portion.

13. The method of ionizing air of claim 11, wherein the external electrode circumscribes an angle of greater than 180° of the anode.

14. The method of ionizing air of claim 11, further comprising lacing the bipolar ionization device into an HVAC duct.

* * * * *